United States Patent

Quick et al.

[11] 4,347,361
[45] Aug. 31, 1982

[54] 4,5α-EPOXY-3-HYDROXY OR METHOXY-7-(1-HYDROXY-ALKYL OR 1-OXOALKYL)MORPHINAN-6-ONE COMPOUNDS

[75] Inventors: James E. Quick, Lexington; Raj K. Razdan, Belmont; Haldean C. Dalzell, Weston, all of Mass.

[73] Assignee: SISA, Incorporated, Cambridge, Mass.

[21] Appl. No.: 215,051

[22] Filed: Dec. 10, 1980

[51] Int. Cl.³ .................. C07D 489/02; A61K 31/485
[52] U.S. Cl. ......................................... 546/45; 424/260
[58] Field of Search ..................... 546/45, 44

[56] References Cited

U.S. PATENT DOCUMENTS 3,433,791  3/1969  Bentley ............................... 546/39
3,488,354  1/1970  Brown et al. ........................ 546/39

OTHER PUBLICATIONS

Kotick et al., J. Med. Chem., vol. 23, No. 2, pp. 166–174 (02/80).
Stork et al., J. Am. Chem. Soc., vol. 75, pp. 4373–4374 (1953).
Lester et al., Chemical Abstracts, vol. 61, 5705h–5707f (1964).

*Primary Examiner*—Anton H. Sutto
*Assistant Examiner*—Diana G. Rivers
*Attorney, Agent, or Firm*—Jerome L. Jeffers

[57] ABSTRACT

Disclosed are 4,5α-epoxy-3-hydroxy or methoxy-7-(1-hydroxyalkyl or 1-oxoalkyl)morphinan-6-one compounds characterized by the structural formulae:

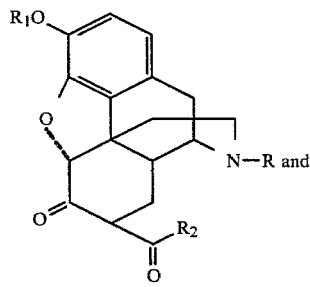

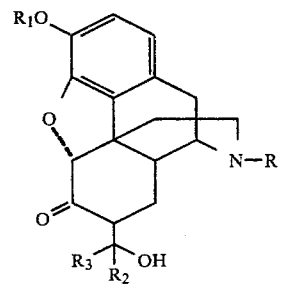

In the foregoing formulae R is methyl, cyclopropylmethyl, cyclobutylmethyl, propargyl, allyl, dimethylallyl, cis-chloroallyl or furfuryl; $R_1$ is H or methyl; $R_2$ is straight or branched chain alkyl of from 1 to 10 carbon atoms, aryl, substituted aryl or arylalkyl, in which the alkyl group contains from 1 to 6 carbon atoms, and $R_3$ is a straight chain alkyl of 1 to 4 carbon atoms.

23 Claims, No Drawings

4,5α-EPOXY-3-HYDROXY OR METHOXY-7-(1-HYDROXY-ALKYL OR 1-OXOALKYL)MORPHINAN-6-ONE COMPOUNDS

BACKGROUND OF THE INVENTION

Certain well known narcotic analgesics belong to the class of 4,5α-epoxymorphinan compounds which have the following basic ring system, in which the atoms are numbered as indicated.

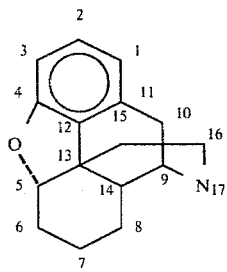

(I)

The two most familiar compounds of this class are morphine and its 3-methyl ether, codeine, with the structures indicated below.

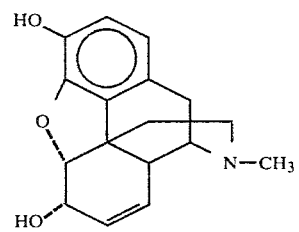

(II)
Morphine

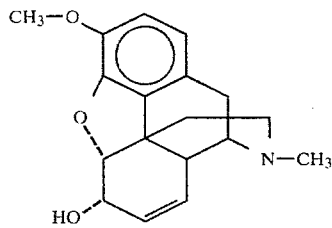

(III)
Codeine

When the 6-hydroxyl group of each of these compounds is oxidized to an oxo group, the compounds conveniently are referred to as morphinone and codeinone, respectively. When the N-methyl groups of the latter compounds are replaced by other substituent groups they may be referred to as N-substituted normorphinones and norcodeinones, respectively. There are two types of nomenclature commonly used for describing compounds herein. The trivial names, such as morphine or morphinone, are widely accepted and used for the sake of brevity and clarity. The Chemical Abstracts nomenclature is preferred and is used whereever precision is needed.

Morphine and its relatives are used primarily for the relief of pain (i.e., as analgesics). They are narcotic and possess dependence-inducing ability and produce other side effects that make them less than ideal analgesics (emesis, constipation, sweating, respiratory depressions, miosis). A compound with the appropriate profile of analgesic (agonist) and narcotic antagonist actions which is not morphine-like has potential as an analgesic agent for treatment of moderate to severe pain without liability of drug dependence. Furthermore, a compound having only strong narcotic antagonist action may be a desirable agent for treatment of drug dependence.

Bentley and Hardy disclose in Journal of the American Chemical Society, 89:13, Pp. 3267-73 certain Diels-Alder adducts of thebaine having the formula:

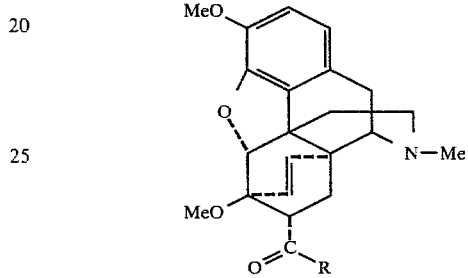

where R is methyl or phenyl. It is stated that these compounds possess analgesic activity. The 6,14-endoethenotetrahydrothebaine (oripavine) series of analgesics as disclosed by Bentley and his coworkers differs from the present series by the presence of the 6,14-ethenobridge in the oripavines. This bridge alters the stereochemistry of the molecules. Furthermore, the oripavines contain a methyl ether of a tertiary alcohol at C-6 whereas the present series contains a keto group at that position. No specific data on the analgesic activity of the 7-acyl oripavines are given. The analgesic activity of the side chain tertiary alcohols in the oripavine series generally increases through $R=C_3H_7$ and then decreases. The morphine antagonist activity for the $N-CH_2-cC_3H_5$ derivatives decreases with the increase in the size of R.

SUMMARY OF THE INVENTION

The present invention involves 4,5α-epoxy-3-hydroxy or methoxy-7-(1-hydroxyalkyl or 1-oxoalkyl)-morphinan-6-one compounds characterized by the structural formulae:

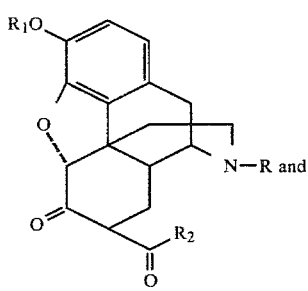

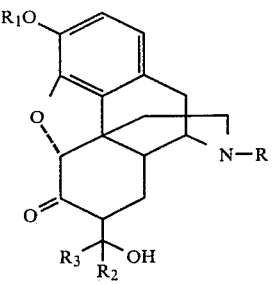

In the foregoing formulae R is methyl, cyclopropylmethyl, cyclobutylmethyl, propargyl, allyl, dimethylallyl, cis-chloroallyl, or furfuryl; $R_1$ is H or methyl; $R_2$ is straight or branched chain alkyl of from 1 to 10 carbon atoms, aryl, substituted aryl or arylalkyl in which the alkyl chain contains from 1 to 6 carbon atoms and $R_3$ is a straight chain alkyl group of 1 to 4 carbon atoms.

DETAILED DESCRIPTION

The preparation of the compounds of the present invention is outlined in Scheme I.

SCHEME I

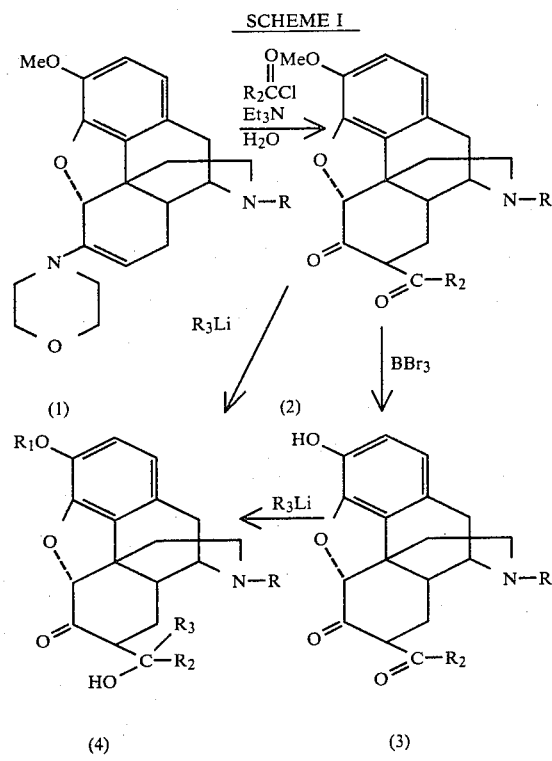

Referring to Scheme I, Compound (2) is prepared by reacting Compound (1) [I. Seki, Yagugaku Zasshi 84, 615 (1964) CA: 61:9544 (1964)] where R is methyl, cyclopropylmethyl, cyclobutylmethyl, propargyl, allyl, dimethylallyl, cis-chloroallyl, furfuryl with an acyl chloride in the presence of triethylamine followed by treatment with water.

Suitable acyl halides include compounds of the formula:

in which $R_2$ is a straight or branched chain alkyl of 1 to 10 carbon atoms, e.g., methyl, ethyl, propyl, isopropyl, pentyl, heptyl or decyl; aryl, e.g., phenyl, naphthyl and heteroaryls including furanyl; or substituted aryl, e.g., p-fluorophenyl, trimethylphenyl, nitrophenyl and methoxyphenyl; and arylalkyl, e.g., phenethyl. The reaction is carried out in a suitable inert solvent, such as benzene, toluene and the halogenated hydrocarbons chloroform and trichloroethylene with or without the addition of an organic base at a temperature in the range of from 25° C. to 150° C. for a period sufficient to form the desired intermediate which is converted to Compound (2) by adding water to the reaction medium. Recovery and purification of Compound (2) is accomplished by treatment with base, followed by extraction and chromatographic purification. Compound (2) is converted to Compound (3) (its 3-hydroxy counterpart) by reaction with boron tribromide in a suitable inert solvent at room temperature. The compounds of Formula 2 and 3 are important in that they can be converted to the tertiary alcohol 4 by the addition of an alkyl lithium reagent of the formula $R_3Li$ where $R_3$ is a straight chain alkyl group of 1 to 4 carbon atoms. This reaction is carried out in a suitable solvent such as tetrahydrofuran, diethyl ether or dimethoxyethane at a temperature of from $-90°$ to $+25°$ C. We have found temperatures on the order of $-78°$ C. to be preferable.

Certain of the compounds corresponding to Formulae 2, 3 and 4 have been found to have analgesic activity, narcotic antagonist activity or a combination of these activities which render them useful as nonaddictive strong analgesics.

The preparation of the morphinan compounds of the present invention is further illustrated by the following examples.

EXAMPLE I

Preparation of 7-(4-Phenylbutyroyl)Dihydrocodeinone

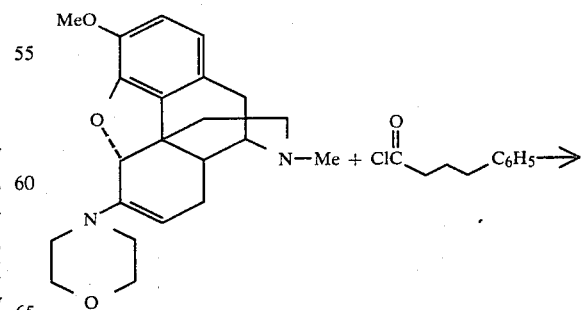

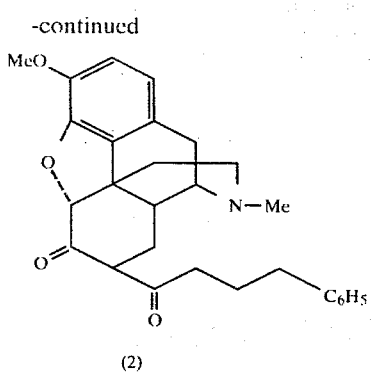

(2)

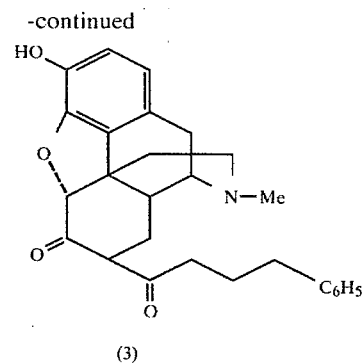

(3)

To a cooled solution of 6 g. of the morpholine enamine of dihydrocodeinone (1) in 5.6 g. of dry triethylamine and 350 ml. of trichloroethylene was slowly added 10.04 g. of 4-phenylbutyroyl chloride in 50 ml. of trichloroethylene. After 1.5 hr. the ice bath was replaced with a heating bath and the solution was refluxed for 8.5 hr. then allowed to stir at room temperature overnight.

After addition of 100 ml. of water the mixture was refluxed for 2 hr. After cooling, the mixture was basified with concentrated ammonium hydroxide whereupon the aqueous phase was separated and extracted twice with chloroform. The combined organic layers were dried (Na$_2$SO$_4$) and concentrated in vacuo. The residue was dissolved in methanol, and stirred with about 10 g. of solid potassium carbonate for 5.5 hr. The solution was filtered and concentrated in vacuo and the residue partitioned between diethyl ether and water. The aqueous layer was extracted three times with diethyl ether at which point the combined ether layers were dried (Na$_2$SO$_4$) and concentrated to afford 14.2 g. of an oil. Chromatography of this oil on 300 g. of silica gel afforded 3.40 g. (49% yield) of 7-(4-phenylbutyroyl)dihydrocodeinone (2) upon elution with graded methanol-chloroform mixtures. Recrystallization from ethanol afforded a solid melting at 170°–171.5° C.

Anal. Calc. for C$_{20}$H$_3$NO$_4$: C, 75.48; H, 7.01; N, 3.14. Found: C, 75.46; H, 7.08; N, 3.12.

Mass Spec. (m/e) 445 (M+).

EXAMPLE II

Preparation of 7-(4-Phenylbutyroyl)Dihydromorphone

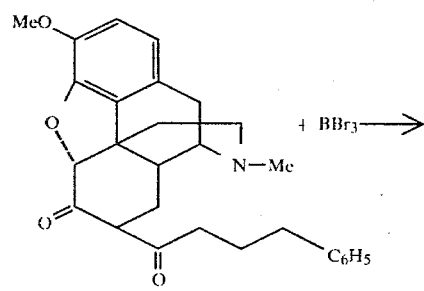

(2)

To a solution of 8.9 ml. of boron tribromide in 150 ml. of chloroform was added, dropwise, a solution of 3.4 g. 7-(4-phenylbutyroyl)dihydrocodeinone (2) in 100 ml. of chloroform. After stirring for one additional hour, the reaction mixture was quenched by pouring it into a stirred mixture of ice and concentrated ammonium hydroxide (1:1). After stirring for 1 hr. the aqueous layer was separated and extracted twice with chloroform. The combined chloroform layers were dried (Na$_2$SO$_4$) and concentrated in vacuo to afford 3.5 g. of a gummy solid. This material was chromatographed on 90 g. of silica gel. Elution with graded methanol-chloroform mixtures afforded 2.19 g. (65% yield) of 7-(4-phenylbutyroyl)dihydrobromorphone (3).

The material forms a hydrochloride salt which decomposes at 175° C.

Mass spec. (m/e) 431 (M+; free base).

EXAMPLE III

Preparation of 17-Cyclopropylmethyl-4,5α-Epoxy-3-Hydroxy-7-(1-Hydroxy-1-Methylbutyl)Morphinan-6-One

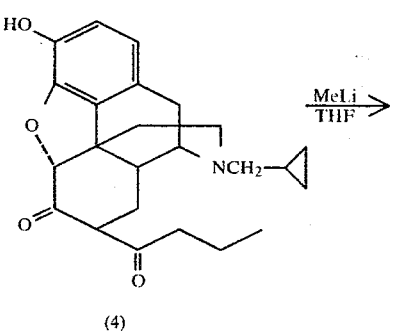

(4)

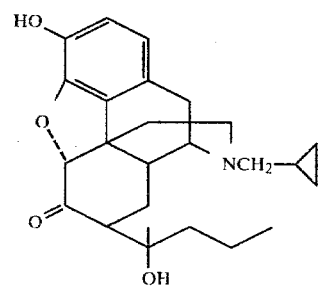

(5)

To 375 mg. of 17-cyclopropylmethyl-4,5α-epoxy-3-hydroxy-7-butanoylmorphinan-6-one (4) in 10 ml. of dry tetrahydrofuran at −78° C. was added, dropwise, 6 ml. of 1.6 M methyl lithium. The mixture was then allowed to warm slowly (over 2 hr.) to −55° C. The mixture was then quenched by the sequential addition of moist diethyl ether and saturated aqueous ammonium chloride. After acidification with acetic acid and rebasification with ammonium hydroxide the aqueous solution was extracted with chloroform. The organic layer was dried ($Na_2SO_4$) and concentrated to afford 362 mg. of crude oil. Chromatography on 8 g. of silica gel with graded methanol-chloroform mixtures afforded a fraction rich in (5) which was purified further by preparative tlc to afford 121 mg. (29%) of 17-cyclopropylmethyl-4,5α-epoxy-3-hydroxy-7-(1-hydroxy-1-methylbutyl)morphinan-6-one as a glassy foam.

Mass spec. (m/e) 411 ($M^+$); 393 ($M^+ - 18$).

Other compounds within the scope of the present invention are prepared by the procedure of the examples using the appropriate starting materials. The physical characteristics of these compounds, whose structures can be determined by reference to Tables I and II, supra, are set out in the following table.

PHYSICAL DATA ON COMPOUNDS OF THIS INVENTION

| Compound | Free Base mp (°C.) | MW | Mass spec M+ (m/e) | FORMULA (free base or HCl salt) | Analysis Calculated C | H | N | Found C | H | N | HCl salt mp(°C.) |
|---|---|---|---|---|---|---|---|---|---|---|---|
| TR 5463 | 164–5 | 381 | | $C_{23}H_{27}NO_4$ | 72.42 | 7.13 | 3.61 | 72.34 | 7.14 | 3.67 | |
| TR 5475 | 135 | 367 | 367 | $C_{22}H_{25}NO_4.0.5CH_3OH$ | 70.46 | 7.11 | 3.65 | 70.92 | 6.92 | 3.72 | |
| TR 5570 | | 395 | 395 | $C_{24}H_{29}NO_4.HCl.2H_2O$ | 61.50 | 7.33 | 2.97 | 60.86 | 6.53 | 2.96 | 170(dec) |
| TR 5573 | | 381 | | $C_{23}H_{27}NO_4.HCl.2H_2O$ | 60.84 | 7.12 | 3.08 | 59.71 | 6.42 | 3.05 | 215(dec) |
| TR 5464 | | 409 | | $C_{25}H_{31}NO_4.HCl.H_2O$ | 64.71 | 7.39 | 3.02 | 64.81 | 7.00 | 3.04 | 155 |
| TR 5476 | | 393 | | $C_{24}H_{29}NO_4.HCl.H_2O$ | 64.05 | 7.18 | 3.11 | 64.01 | 7.20 | 3.09 | |
| TR 5519 | | 423 | | $C_{26}H_{33}NO_4.HCl.0.5H_2O$ | 66.56 | 7.52 | 2.99 | 66.41 | 7.55 | 2.99 | |
| TR 5520 | | 409 | | $C_{25}H_{31}NO_4.HCl$ | 67.33 | 7.23 | 3.14 | 67.13 | 7.30 | 3.13 | >240 |
| TR 5504 | | 437 | | $C_{27}H_{35}NO_4.HCl.H_2O$ | 65.89 | 7.80 | 2.85 | 66.04 | 7.43 | 2.86 | 135 |
| TR 5505 | | 423 | | $C_{26}H_{33}NO_4.HCl.H_2O$ | 65.32 | 7.61 | 2.93 | 65.26 | 7.59 | 2.91 | 190(dec) |
| TR 5539 | | 451 | | $C_{28}H_{37}NO_4.HCl.0.5H_2O$ | 67.64 | 7.92 | 2.82 | 68.09 | 7.79 | 2.81 | |
| TR 5540 | | 437 | 437 | $C_{27}H_{35}NO_4.HCl.0.5H_2O$ | 67.13 | 7.72 | 2.90 | 67.08 | 7.75 | 2.90 | 175 |
| TR 5509 | | 409 | 409 | $C_{25}H_{31}NO_4.HCl.H_2O$ | 64.70 | 7.40 | 3.02 | 67.86 | 6.89 | 2.92 | 190(dec) |
| TR 5511 | | 395 | 395 | $C_{24}H_{29}NO_4.HCl.H_2O$ | 64.05 | 7.18 | 3.11 | 62.64 | 6.78 | 2.95 | |
| TR 5571 | | 437 | | $C_{27}H_{35}NO_4.HCl.H_2O$ | 65.90 | 7.78 | 2.84 | 65.84 | 7.25 | 2.94 | 170(dec) |
| TR 5574 | | 423 | | $C_{26}H_{33}NO_4.HCl.H_2O$ | 65.32 | 7.59 | 2.93 | 65.29 | 7.60 | 2.93 | 213–5 |
| TR 5577 | | 457 | 457 | $C_{29}H_{31}NO_4.HCl$ (contains some pyrone) | 70.50 | 6.53 | 2.84 | 69.22 | 6.18 | 2.40 | 167–70 |
| TR 5506 | | 429 | 429 | $C_{27}H_{27}NO_4.HCl$ | | | | | | | |
| TR 5501 | | 443 | 443 | $C_{28}H_{29}NO_4.HCl.H_2O$ | 66.45 | 6.19 | 2.77 | 67.53 | 6.30 | 3.72 | 140 |
| TR 5579 | 155–7 | 447 | | $C_{27}H_{26}FNO_4$ | 72.47 | 5.96 | 3.13 | 72.37 | 5.88 | 3.10 | |
| TR 5575 | | 461 | 461 | $C_{28}H_{28}FNO_4.HCl.H_2O$ | 65.16 | 6.07 | 2.71 | 64.53 | 5.76 | 2.67 | 178–80 |
| TR 5649 | (dec) 145 | 428 | | $C_{25}H_{25}NO_5.0.5H_2O$ | 70.07 | 6.12 | 3.27 | 70.11 | 6.18 | 3.27 | |
| TR 5634 | | 433 | | $C_{26}H_{27}NO_5.HCl.1.5H_2O$ | 62.83 | 6.29 | 2.82 | 62.86 | 6.32 | 2.82 | 186–8 |
| MLS 5695H | | 355 | 355 | $C_{21}H_{25}NO_4.HCl.H_2O$ | 61.53 | 6.89 | 3.41 | 61.30 | 6.88 | 3.41 | |
| MLS 5689H | | 383 | 383 | $C_{23}H_{29}NO_4.HCl$—$0.6CHCl_3$ | 57.65 | 6.28 | 2.85 | 57.61 | 6.50 | 3.05 | 160(dec) |
| MLS 5690H | | 417 | 417 | $C_{26}H_{27}NO_4.HCl$—$0.5CHCl_3$ | 61.96 | 5.60 | 2.73 | 61.39 | 5.77 | 2.85 | 175(dec) |
| MLS 5691H | | 431 | 431 | $C_{27}H_{24}NO_4.HCl.0.7CHCl_3$ | 60.31 | 5.62 | 2.54 | 60.41 | 5.93 | 2.66 | 175(dec) |
| MLS 5692 | 160–1.5 | 369 | 369 | $C_{22}H_{27}NO_4.0.25H_2O$ | 70.56 | 7.53 | 3.74 | 70.60 | 7.64 | 3.88 | |
| MLS 5682 | 155–6 | 397 | | $C_{24}H_{31}NO_4$ | 72.51 | 7.86 | 3.52 | 72.44 | 7.86 | 3.52 | |
| MLS 5683 | 170–1.5 | 445 | | $C_{28}H_{31}NO_4$ | 75.48 | 7.01 | 3.14 | 75.46 | 7.08 | 3.12 | |

PHYSICAL DATA ON COMPOUNDS OF THIS INVENTION —continued

| Compound | mp (°C.) | Free Base MW | Mass spec M+ (m/e) | FORMULA (free base or HCl salt) | Analysis Calculated C | H | N | Found C | H | N | HCl salt mp(°C.) |
|---|---|---|---|---|---|---|---|---|---|---|---|
| 5688H TR | | 431 | 431 | $C_{27}H_{29}NO_4.HCl.H_2O$ | 66.71 | 6.65 | 2.88 | 67.30 | 6.71 | 2.91 | (125(dec) |
| 5492 TR | oil | 357 | 357 | $C_{21}H_{27}NO_4$ | | | | | | | |
| 5479 TR | oil | 397 | 397 | $C_{24}H_{31}NO_4$ | | | | | | | |
| 5499 TR | foam | 425 | 425 | $C_{26}H_{35}NO_4.0.2CHCl_3$ | 70.20 | 7.90 | 3.12 | 70.14 | 7.81 | 3.28 | |
| 5544 TR | foam | 439 | 439 | $C_{27}H_{37}NO_4$ | 73.76 | 8.50 | 3.19 | 72.83 | 8.35 | 3.06 | |
| 5543 TR | foam | 411 | 411 | $C_{25}H_{33}NO_4.0.3CHCl_3$ | 67.90 | 7.51 | 3.13 | 67.84 | 7.54 | 3.17 | |
| 5551 TR | 134–7 | 425 | 425 | $C_{26}H_{35}NO_4$ | 73.38 | 8.29 | 3.29 | 71.47 (reverse aldol on heating) | 7.37 | 3.79 | |
| 5538 TR | foam | 439 | 439 | $C_{27}H_{27}NO_4.0.1CHCl_3$ | 72.07 | 8.30 | 3.10 | 72.43 | 8.29 | 3.27 | |
| 5572 MLS | 195–7 | 411 | 411 | $C_{25}H_{33}NO_4.0.4CHCl_3$ | 66.40 | 7.34 | 3.05 | 65.77 | 7.52 | 2.45 | |
| 5694 | 194–5 | 399 | 399 | $C_{24}H_{33}NO_4$ | 72.15 | 8.33 | 3.51 | 72.04 | 8.33 | 3.47 | |

PHARMACOLOGICAL EVALUATION

The compounds whose preparation is disclosed in the foregoing examples were screened to determine the following biological activities:

(A) Analgesic effects upon mice (acetic acid writhing test).
(B) Narcotic antagonist activity in rats (modified rat tail flick test).

TEST A. ACETIC ACID MOUSE WRITHING TEST

The analgesic effects of test compounds were determined in mice by use of the acetic acid writhing test described by B. A. Whittle, Brit. J. Pharmacol., 22:246 (1964). In this test at least three groups of five male CD-1 mice each were given subcutaneous doses of the test drug dissolved in either distilled water or distilled water acidified with HCl depending on the solubility of the compound. Fifteen (15) minutes post drug, 0.4 milliliter of a 0.75% or 1.0% or 0.6 milliliter of a 1.0% V/V acetic acid in distilled water solution was administered intraperitoneally. The number of writhes in a 20 minute interval beginning 5 minutes after the acetic acid injection were determined and compared with the number of writhes in control groups which had received only acetic acid.

Percent inhibition of writhing was calculated as:

$$\% \text{ inhibition} = \frac{\text{No. control writhes} - \text{No. treated writhes}}{\text{No. control writhes}}$$

The $ED_{50}$ dose, i.e., the dose required to reduce the number of writhes by 50%, was determined graphically from a plot of % inhibition as a probit versus log dose. Confidence limits of 95% were calculated on the basis of those results falling in the range 16–84% inhibition. See Litchfield, J. T. and Wilcoxon, F., J. Pharmacol. Exp. Ther., 96:99, (1949).

TEST B. EVALUATION OF NARCOTIC ANTAGONIST

The narcotic antagonist effects of test compounds were determined by a modification of the rat tail flick procedure of Harris and Pierson, J. Pharmacol. Exp. Ther. 143:141 (1964).

Male albino Wistar rats (100–120 g.) were used for this study. A rat's tail is so placed so as to cover a photocell. Heat is applied by a lamp in a reflector with a timer being connected to the lamp and photocell so that the timer goes on when the light is turned on and is turned off when the photocell is uncovered. A rheostat, incorporated into a heating lamp is used to adjust the intensity of the light falling on the tail of the rat such that the rat's control reaction time is from 1.2 to 5.8 seconds. Animals with a control reaction time outside this range are rejected. The rheostat adjustment is made only if a significant proportion (more than 1 out of every 10 rats) of the reaction times are outside the range of 1.2 to 5.8 seconds. Groups of five rats were used each time, and two control times were determined at least 30 minutes apart.

The test drug was given intraperitoneally and this was followed ten minutes later by an $ED_{80}$ dose of morphine subcutaneously. The animals were retested at 20 minutes after the morphine injection. Control animals were given morphine only. A ten second cutoff time is employed; if the rat does not flick its tail in 10 seconds it is is removed from the heat source. The data were calculated as follows:

$$\% \text{ Effect } (E) = \frac{MRT^*\text{(Treated)} - MRT\text{(Control)} \times 100}{10 - MRT\text{(Control)}}$$

$$\% \text{ Antagonism} = \frac{E\text{(morphine controls)} - E\text{(drug treated)} \times 100}{E\text{(morphine control)}}$$

*MRT is defined as Mean Reaction Time.

The data were plotted on log-probit paper and $AD_{50}$ values, i.e., the dose required to inhibit the morphine effect by 50% within 95% confidence limits, were determined by the method of Litchfield and Wilcoxon.

The 4,5α-epoxy-3-hydroxy or methoxy-7-(1-hydroxyalkyl)morphinan-6-one data is tabulated in Table I whereas Table II sets out the data for the 1-hydroxyalkyl compounds. In the following tables CPM means "cyclopropylmethyl", NDR means "no dose response" and the designation X% (Y) means that the number of writhes were reduced by X% at a dosage of Y mg/kg.

TABLE I

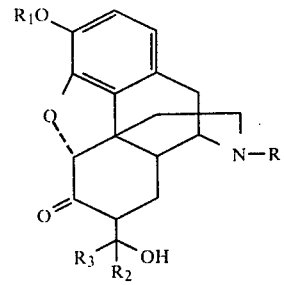

| Compound | R | $R_1$ | $R_2$ | $ED_{50}$ (mg/kg) | $AD_{50}$ (mg/kg) |
|---|---|---|---|---|---|
| TR-5463 | CPM | $CH_3$ | $CH_3$ | 9%(10) | Ia(10) |
| TR-5475 | CPM | H | $CH_3$ | 4.05 | 1.3 |
| TR-5570 | CPM | $CH_3$ | $C_2H_5$ | 11%(10) | 6.5 |
| TR-5573 | CPM | H | $C_2H_5$ | Ia(10) | 0.51 |
| TR-5464 | CPM | $CH_3$ | $C_3H_7$ | 2.81 | 8.1 |
| TR-5476 | CPM | H | $C_3H_7$ | 4.65 | 2.55 |
| TR-5519 | CPM | $CH_3$ | $C_4H_9$ | >10.0 | Ia(10) |
| TR-5520 | CPM | H | $C_4H_9$ | 1.59 | 77%(10) |
| TR-5504 | CPM | $CH_3$ | $C_5H_{11}$ | 5.7 | Ia(10) |
| TR-5505 | CPM | H | $C_5H_{11}$ | 0.29 | 22 |
| TR-5539 | CPM | $CH_3$ | $C_6H_{13}$ | >10.0 | >10.0 |
| TR-5540 | CPM | H | $C_6H_{13}$ | 0.4 | Ia(10) |
| TR-5509 | CPM | $CH_3$ | $i\text{-}C_3H_7$ | 7.5 | 2.8 |
| TR-5511 | CPM | H | $i\text{-}C_3H_7$ | >10 | 0.81 |
| TR-5571 | CPM | $CH_3$ | $t\text{-}C_4H_9$ | Ia(10) | 13%(10) |
| TR-5574 | CPM | H | $CH_2t\text{-}C_4H_9$ | Ia(10) | >10 |
| TR-5577 | CPM | $CH_3$ | $CH_2C_6H_5$ | 21%(10) | Ia(10) |
| TR-5506 | CPM | H | $C_6H_5$ | 4.35 | 0.24 |
| TR-5501 | CPM | $CH_3$ | $C_6H_5$ | 11.3 | 8.0 |
| TR-5579 | CPM | H | $C_6H_4\text{—}pF$ | 29%(10) | 45%(10) |
| TR-5575 | CPM | $CH_3$ | $C_6H_4\text{—}pF$ | Ia(10) | 17%(10) |
| TR-5649 | CPM | H | $C_4H_3O$ | 28%(10) | NDR |
| TR-5634 | CPM | $CH_3$ | $C_4H_3O$ | 14%(10) | 3.95 |
| MLS-5692 | $CH_3$ | $CH_3$ | $C_3H_7$ | Ia(10) | — |
| MLS-5695 | $CH_3$ | H | $C_3H_7$ | 5.25 | — |
| MLS-5682 | $CH_3$ | $CH_3$ | $C_5H_{11}$ | 4.0 | — |
| MLS-5689 | $CH_3$ | H | $C_5H_{11}$ | 0.76 | — |
| MLS-5688H | $CH_3$ | $CH_3$ | $(CH_2)_2\text{—}C_6H_5$ | 0.62 | — |
| MLS-5690 | $CH_3$ | H | $(CH_2)_2\text{—}C_6H_5$ | 0.105 | — |
| MLS-5683 | $CH_3$ | $CH_3$ | $(CH_2)_3\text{—}C_6H_5$ | 0.41 | — |
| MLS-5691 | $CH_3$ | H | $(CH_2)_3\text{—}C_6H_5$ | 0.0052 | — |

TABLE II

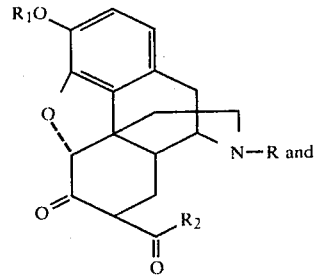

| Compound | R | $R_1$ | $R_3$ | $R_2$ | $ED_{50}$ (mg/kg) | $AD_{50}$ (mg/kg) |
|---|---|---|---|---|---|---|
| TR-5492 | $CH_3$ | $CH_3$ | $CH_3$ | $CH_3$ | 4.5 | — |
| TR-5479 | CPM | $CH_3$ | $CH_3$ | $CH_3$ | Ia(10) | 41%(10) |
| TR-5499 | CPM | $CH_3$ | $CH_3$ | $C_3H_7$ | 0.42 | 12%(7) |

TABLE II-continued

| Compound | R | $R_1$ | $R_3$ | $R_2$ | $ED_{50}$ (mg/kg) | $AD_{50}$ (mg/kg) |
|---|---|---|---|---|---|---|
| TR-5544 | CPM | $CH_3$ | $CH_3$ | $C_4H_9$ | 10%(10) | Ia(10) |
| TR-5543 | CPM | H | $CH_3$ | $C_3H_7$ | 1.8 | 2.8 |
| TR-5551 | CPM | H | $CH_3$ | $C_4H_9$ | 40%(10) | 2.5 |
| TR-5538 | CPM | H | $CH_3$ | $C_5H_{11}$ | 0.28 | 6.6 |
| TR-5572 | CPM | H | $CH_3$ | $i\text{-}C_3H_7$ | 7.8 | 2.2 |
| MLS-5694 | $CH_3$ | H | $C_5H_{11}$ | $CH_3$ | 2.9 | — |

What is claimed is:

1. 4,5α-epoxy-3-hydroxy or methoxy-7-(1-hydroxyalkyl or 1-oxoalkyl)morphinan-6-one compounds characterized by the structural formulae:

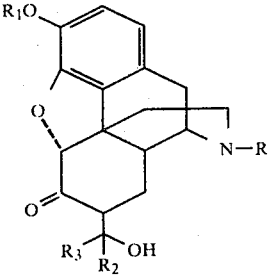

wherein R is methyl, cyclopropylmethyl, cyclobutylmethyl, propargyl, allyl, dimethylallyl, cis-chloroallyl or furfuryl; $R_1$ is H or methyl; $R_2$ is straight or branched chain alkyl of from 1 to 10 carbon atoms, phenyl or phenylalkyl in which the alkyl chain contains from 1 to 6 carbon atoms, and $R_3$ is a straight chain alkyl of 1 to 4 carbon atoms.

2. The compounds of claim 1 which are characterized by the formula:

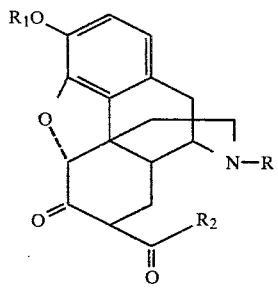

wherein R, $R_1$ and $R_2$ are as previously defined.

3. A compound as defined by claim 2 wherein R is cyclopropylmethyl, $R_1$ is H and $R_2$ is $CH_3$.

4. A compound as defined by claim 2 wherein R is cyclopropylmethyl, $R_1$ is $CH_3$ and $R_2$ is $C_3H_7$.

5. A compound as defined by claim 2 wherein R is cyclopropylmethyl, $R_1$ is H and $R_2$ is $C_3H_7$.

6. A compound as defined by claim 2 wherein R is cyclopropylmethyl, $R_1$ is $CH_3$ and $R_2$ is i-$C_3H_7$.

7. A compound as defined by claim 2 wherein R is cyclopropylmethyl, $R_1$ is H and $R_2$ is $C_6H_5$.

8. A compound as defined by claim 2 wherein R is cyclopropylmethyl, $R_1$ is $CH_3$ and $R_2$ is $C_6H_5$.

9. A compound as defined by claim 2 wherein R is cyclopropylmethyl, $R_1$ is H and $R_2$ is $C_2H_5$.

10. A compound as defined by claim 2 wherein R is cyclopropylmethyl, $R_1$ is H and $R_2$ is $C_4H_9$.

11. A compound as defined by claim 2 wherein R is cyclopropylmethyl, $R_1$ is H and $R_2$ is $C_5H_{11}$.

12. A compound as defined in claim 2 wherein R is cyclopropylmethyl, $R_1$ is H and $R_2$ is $C_6H_{13}$.

13. A compound as defined in claim 2 wherein R is cyclopropylmethyl, $R_1$ is H and $R_2$ is i-$C_3H_7$.

14. A compound as defined in claim 2 wherein R is $CH_3$, $R_1$ is H and $R_2$ is $C_5H_{11}$.

15. A compound as defined in claim 2 wherein R is $CH_3$, $R_1$ is $CH_3$ and $R_2$ is $(CH_2)_2$—$C_6H_5$.

16. A compound as defined in claim 2 wherein R is $CH_3$, $R_1$ is H and $R_2$ is $(CH_2)_2$—$C_6H_5$.

17. A compound as defined in claim 2 wherein R is $CH_3$, $R_1$ is $CH_3$ and $R_2$ is $(CH_2)_3$—$C_6H_5$.

18. A compound as defined in claim 2 wherein R is $CH_3$, $R_1$ is H and $R_2$ is $(CH_2)_3$—$C_6H_5$.

19. The compounds of claim 1 which are characterized by the formula:

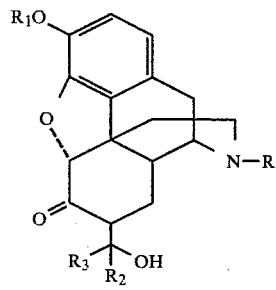

wherein R, $R_1$, $R_2$ and $R_3$ are as previously defined.

20. A compound as defined by claim 19 wherein R is cyclopropylmethyl, $R_1$ is H, $R_2$ is $C_3H_7$ and $R_3$ is $CH_3$.

21. A compound as defined by claim 19 wherein R is cyclopropylmethyl, $R_1$ is H, $R_2$ is $C_5H_{11}$ and $R_3$ is $CH_3$.

22. A compound as defined by claim 19 wherein R is cyclopropylmethyl, $R_1$ is H, $R_2$ is i-$C_3H_7$ and $R_3$ is $CH_3$.

23. A compound as defined by claim 19 wherein $R_1$ is cyclopropylmethyl, $R_1$ is $CH_3$, $R_2$ is $C_3H_7$ and $R_3$ is $CH_3$.

* * * * *